United States Patent [19]

Braish

[11] Patent Number: 5,153,350
[45] Date of Patent: Oct. 6, 1992

[54] PROCESS FOR PREPARING 3,4,6-TRIFLUOROPHTHALONITRILE

[76] Inventor: Tamim F. Braish, Eastern Point Rd., Groton, Conn. 06340

[21] Appl. No.: 701,280

[22] Filed: May 16, 1991

[51] Int. Cl.$^5$ .................. C07C 253/30; C07C 255/51
[52] U.S. Cl. .................................... 558/419; 558/425
[58] Field of Search ............................. 558/419, 425

[56] References Cited

U.S. PATENT DOCUMENTS

| | | | |
|---|---|---|---|
| 3,290,353 | 12/1966 | Battershell et al. | 558/419 OR |
| 3,312,746 | 4/1967 | Fielding | 558/419 X |
| 3,816,505 | 6/1974 | Watts, Jr. | 558/419 OR |
| 3,887,581 | 6/1975 | Kinoshita et al. | 260/325 |
| 3,975,424 | 8/1976 | Fujii et al. | 558/419 OR |
| 4,209,457 | 6/1980 | Fuller | 5587/425 OR |
| 4,229,365 | 10/1980 | Oeser et al. | 558/425 OR |
| 4,684,734 | 8/1987 | Kaieda et al. | 558/425 OR |
| 4,925,966 | 5/1990 | Kobayashi et al. | 558/419 OR |

FOREIGN PATENT DOCUMENTS

| | | |
|---|---|---|
| 51-6940 | 1/1976 | Japan . |
| 1-52737 | 2/1989 | Japan . |
| 1-160944 | 6/1989 | Japan . |
| 1-258639 | 10/1989 | Japan . |
| 2-000154 | 1/1990 | Japan ................................... 558/419 |
| 2-117643 | 5/1990 | Japan ................................... 558/419 |
| 1026290 | 4/1966 | United Kingdom ................ 558/419 |

OTHER PUBLICATIONS

Fieser & Fieser, Reagents for Organic Synthesis, (1967), pp. 1278-1280.
Fieser & Fieser, Reagents for Organic Synthesis, (1975), pp. 757.
Tashiro, et al.; J. Org. Chem., 42, (1977), pp. 835-838.
Colon, J. Org. Chem., 47, (1982), pp. 2622-2625.
Al-Fakhri, K., et al., J.C.S. Chem. Comm., 1980, pp. 566-568.

Primary Examiner—Joseph Paul Brust
Attorney, Agent, or Firm—Peter C. Richardson; J. Trevor Lumb; Mervin E. Brokke

[57] ABSTRACT

A process for preparing 3,4,6-trifluorophthalonitrile from 3,4,5,6-tetrachlorophthalonitrile comprising the sequential steps of reductively dechlorinating the tetrachlorophthalonitrile, in the presence of a metal in an aqueous acidic medium, to produce 3,4,6-trichlorophthalonitrile and then subjecting the trichlorophthalonitrile to a chlorine-fluorine exchange by reaction with a fluoride source in a polar aprotic solvent.

9 Claims, No Drawings

PROCESS FOR PREPARING 3,4,6-TRIFLUOROPHTHALONITRILE

BACKGROUND OF THE INVENTION

The present invention relates to a process for the synthesis of 3,4,6-trifluorophthalonitrile. This compound is a useful intermediate in the synthesis of 2,4,5-trifluorobenzoic acid which, in turn, is a starting material for quinolone antibiotics such as those disclosed in U.S. Pat. Nos. 4,571,396 and 4,861,779.

The synthesis of 2,4,5-trifluorobenzoic acid from 3,4,6-trifluorophthalic acid has been reported in Japanese Kokai Patent SHO 64-52737. Japanese Kokai Patent Hei 1-258639 discloses a process for preparing 2,4,5-trifluorobenzoic acid from 2,4,5,6-tetrafluoroisophthalonitrile wherein the first step comprises reductive defluorination to 2,4,5-trifluoroisophthalonitrile.

A method for the preparation of 3,4,6-trifluorophthalonitrile from 3,4,5,6-tetrafluorophthalonitrile, via reductive defluorination, has been reported in Japanese Kokai Patent Hei 1-160944. In this process, however, the yields are inconsistent and a significant amount of over-reduced material 3,6-difluorophthalonitrile, is produced.

3,4,6-Trichlorophthalonitrile is also known in the art and is disclosed as a starting material for the synthesis of iminoisoindolinone dyes in U.S. Pat. No. 3,887,581. One reported method of product 3,4,6-trichlorophthalonitrile is from 3,4,5,6-tetrachlorophthalonitrile via photolysis in the presence of 1,4-dimethoxybenzene (J.C.S. Chem. Comm., p. 566 (1980)). This process is not convenient for large scale production, however, because both the photochemical reaction and separation from the 1,4-dimethoxybenzene are difficult to perform.

The process of the present invention overcomes the aforementioned problems. For example, the present process is readily amenable to large scale production, as it utilizes readily-available reagents, is easily controlled and produces very little of the over-reduced material.

SUMMARY OF THE INVENTION

The present invention relates to a process for the synthesis of 3,4,6-trifluorophthalonitrile by first reacting 3,4,5,6-tetrachlorophthalonitrile with a metal in the presence of an acid and then treating the resulting 3,4,6-trichlorophthalonitrile with a fluoride source in an appropriate solvent to obtain 3,4,6-trifluorophthalonitrile. Typical metals include zinc, tin, iron, nickel and aluminum, in addition to amalgams and alloys thereof. Typical acids include both organic and inorganic acids such as sulfuric, hydrochloric, nitric, citric, acetic, oxalic, phthalic and benzoic acids. Typical fluoride sources include alkali metal fluorides.

DETAILED DESCRIPTION OF THE INVENTION

The process of the present invention may be represented by the following reaction scheme.

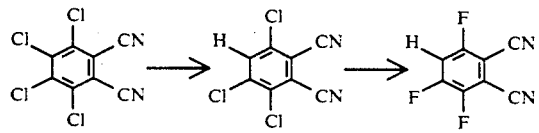

In accordance with the two step process of the invention, 3,4,5,6-tetrachlorophthalonitrile is first reacted with a solid metal, a metal amalgam or an alloy, in a water miscible solvent to give the desired 3,4,6-trichlorophthalonitrile. Examples of solid metals include zinc, tin, iron, nickel and aluminum. Examples of metal amalgams include zinc amalgam, tin amalgam and aluminum amalgam. Examples of alloys include brass, bronze and aluminum-nickel. Preferably, a solid metal is used, with zinc being particularly preferred. Commercially available zinc powder is an exemplary example.

With regard to the relative amounts of the reactants in the first step of the process, the ratio of metal to 3,4,5,6-tetrachlorophthalonitrile will generally range from about 1:1 to about 8:1. Preferably, such as when zinc is used, for example, the ratio will be about 1.5:1.

The reaction is preferably run in a mixture of water and a water miscible solvent. Suitable solvents include, for example, aliphatic alcohols such as methanol, ethanol, glycerol, etc., cyclic ethers such as tetrahydrofuran (THF) and dioxane, and other water miscible solvents such as acetone, acetonitrile, dimethylformamide and dimethylsulfoxide. The most preferred solvent is THF. The ratio of solvent to water will generally range from about 4:1 to about 1:8 and will preferably be about 1:4.

The reaction is carried out in the presence of an acid. Suitable acids include inorganic acids such as sulfuric, hydrochloric and nitric acid and organic acids such as citric, acetic, oxalic, phthalic and benzoic acid. The most preferred acid is sulfuric acid. The concentration of acid used will generally be from about 0.05 to about 10 gram equivalents per gram of 3,4,5,6-tetrachlorophthalonitrile. Preferably, about 0.4 gram equivalents of acid per gram of the nitrile is used.

The reaction can generally be run at temperatures between about 20° C. and 100° C. At these temperatures, the reaction will generally run from about 5 minutes to about 24 hours. Most commonly, a temperature of about 60° C. and a reaction time of about 5 minutes will be utilized.

In the second step of the process, the resulting 3,4,6-trichlorophthalonitrile is treated with a fluoride source in the presence of an appropriate solvent. Preferred fluoride sources include alkali metal fluorides such as sodium, potassium and cesium fluoride. The preferred reagent is spray-dried potassium fluoride.

For this step, the reaction is generally run in a polar aprotic solvent such as dimethylformamide, dimethylsulfoxide, tetramethylene sulfone and N-methylpyrrolidone. Tetramethylene sulfone is the preferred solvent.

Optionally, the reaction can be run in the presence of a phase transfer catalyst such as, for example, tetraalkylammonium halide, tetraalkylphosphonium halide and tetraphenylphosphonium halide. When such phase transfer catalyst is used, tetraphenylphosphonium bromide is preferred.

The reaction can generally be run at temperatures between about 120° C. and 220° C. At these temperatures, the reaction will generally run from about 2 to about 40 hours. Most commonly, a temperature of about 185° C. and a reaction time of about 6 hours will be utilized.

EXAMPLE

Step 1—3,4,6-trichlorophthalonitrile 3,4,5,6-Tetrachlorophthalonitrile (10 g, 37.6 mmol) was suspended in 250 ml of water and 60 ml of THF was added. To the reaction mixture, zinc (7.4 g, 112.8 mmol) and concentrated sulfuric acid (7.5 ml) were added. The reaction mixture was heated to 60° C. for 5 minutes after which the mixture became homogeneous. The mixture was filtered, the THF evaporated and the aqueous layer was extracted with two 120 ml portions of dichloromethane. The combined organic layers were dried and evaporated to give 7.0 g of the title compound, representing an 80% yield. NMR (CDCl$_3$): Singlet at 7.90 ppm.

Step 2—3,4,6-trifluorophthalonitrile

To the product of step 1 (3.0 g, 12.9 mmol) in 30 ml tetramethylene sulfone, was added potassium fluoride (2.63 g, 45.4 mmol) and the reaction mixture was heated to 185° C. for 6 hours, diluted with 50 ml water and extracted twice with 70 ml ethylacetate-hexane (1:1). The combined organic layers were washed three times with water (10 ml) and dried over MgSO$_4$. The solvent was evaporated, leaving 1.76 g of the title compound, representing a 75% yield, m.p. 36°-38° C. NMR (CDCl$_3$): 8.1 ppm (m, 1H).

I claim:

1. A process for preparing 3,4,6-trifluorophthalonitrile from 3,4,5,6-tetrachlorophthalonitrile, comprising the sequential steps of:

reacting said tetrachlorophthalonitrile with a metal selected from the group consisting of zinc, tin, iron, nickel, aluminum, alloys thereof and amalgams thereof in the presence of an aqueous acid selected from the group consisting of sulfuric, hydrochloric, nitric, citric, acetic, oxalic, phthalic and benzoic acids in an aqueous medium to afford 3,4,6-trichlorophthalonitrile; and reacting said trichlorophthalonitrile with an alkali metal fluoride in a polar aprotic solvent.

2. A process according to claim 1 wherein said acid is sulfuric acid.

3. A process according to claim 2 wherein said metal comprises zinc.

4. A process according to claim 3 wherein said solvent comprises tetrahydrofuran.

5. A process according to claim 1 wherein said alkali metal is potassium.

6. A process according to claim 4 wherein said solvent comprises tetramethylene sulfone.

7. A process according to claim 5 wherein said solvent comprises tetramethylene sulfone.

8. A process according to claim 7 wherein said first reaction occurs under conditions including a temperature of about 60° C. and a reaction time of about 5 minutes.

9. A process according to claim 8 wherein said chlorine-fluorine exchange occurs under conditions including a temperature between about 155° C. and about 185° C. and a reaction time of about 6 hours.

* * * * *